United States Patent
Tong et al.

(10) Patent No.: US 10,544,282 B2
(45) Date of Patent: Jan. 28, 2020

(54) HYDROGEN SULFIDE SCAVENGERS FOR POLYMER TREATED ASPHALT

(71) Applicant: ECOLAB USA INC., St. Paul, MN (US)

(72) Inventors: Xiaowei Tong, Sugarland, TX (US); Jennifer L. Sorrells, Houston, TX (US); Prakasa Rao Anantaneni, Richmond, TX (US)

(73) Assignee: ECOLAB USA INC., St. Paul, MN (US)

( * ) Notice: Subject to any disclaimer, the term of this patent is extended or adjusted under 35 U.S.C. 154(b) by 120 days.

(21) Appl. No.: 15/826,408

(22) Filed: Nov. 29, 2017

(65) Prior Publication Data
US 2018/0163021 A1  Jun. 14, 2018

Related U.S. Application Data

(60) Provisional application No. 62/431,676, filed on Dec. 8, 2016.

(51) Int. Cl.
| | |
|---|---|
| *C08K 5/3492* | (2006.01) |
| *C08L 95/00* | (2006.01) |
| *C10C 3/02* | (2006.01) |
| *C08L 85/02* | (2006.01) |
| *C08G 79/04* | (2006.01) |
| *C01B 17/16* | (2006.01) |
| *C07D 251/24* | (2006.01) |
| *C07D 487/18* | (2006.01) |

(52) U.S. Cl.
CPC .......... *C08K 5/3492* (2013.01); *C01B 17/167* (2013.01); *C07D 251/24* (2013.01); *C07D 487/18* (2013.01); *C08G 79/04* (2013.01); *C08L 85/02* (2013.01); *C08L 95/00* (2013.01); *C10C 3/026* (2013.01); *C08L 2555/60* (2013.01); *C08L 2555/80* (2013.01)

(58) Field of Classification Search
CPC ..... C01B 17/167; C01B 25/24; C07D 251/24; C07D 487/18; C08G 79/04; C08K 3/32; C08K 5/3472; C08K 5/3492; C08L 85/02; C08L 95/00; C08L 95/005; C08L 2555/40; C08L 2555/60; C08L 2555/80; C10C 3/026

See application file for complete search history.

(56) References Cited

U.S. PATENT DOCUMENTS

| | | | |
|---|---|---|---|
| 5,000,835 A | 3/1991 | Taylor et al. | |
| 5,213,680 A * | 5/1993 | Kremer | C10G 29/20 208/189 |
| 5,314,672 A | 5/1994 | Vasil | |
| 7,264,786 B2 | 9/2007 | Pakulski et al. | |
| 7,438,877 B2 | 10/2008 | Salma et al. | |
| 7,495,045 B2 | 2/2009 | Buras et al. | |
| 7,713,345 B2 | 5/2010 | Maldonado et al. | |
| 8,211,294 B1 | 7/2012 | Zaid et al. | |
| 8,241,491 B1 | 8/2012 | Zaid et al. | |
| 8,734,637 B2 | 5/2014 | Taylor | |
| 2005/0153846 A1 | 7/2005 | Gatlin | |
| 2005/0238556 A1 | 10/2005 | Pakulski et al. | |
| 2009/0097881 A1 | 4/2009 | Kondoh et al. | |
| 2009/0149577 A1 | 6/2009 | Butler et al. | |
| 2011/0160355 A1 * | 6/2011 | Martin | C08L 95/00 524/68 |
| 2011/0220551 A1 * | 9/2011 | Taylor | B01D 53/1468 208/236 |
| 2014/0171721 A1 | 6/2014 | Bertrand, III | |
| 2014/0209304 A1 * | 7/2014 | Reed | C08F 220/56 166/268 |
| 2016/0289450 A1 | 10/2016 | Mouazen et al. | |
| 2017/0022109 A1 * | 1/2017 | Poland | C08K 5/521 |

FOREIGN PATENT DOCUMENTS

| | | |
|---|---|---|
| AR | 59003 | 3/2008 |
| CN | 102618202 | 8/2012 |
| CN | 104031355 | 9/2014 |
| EP | 2262856 A1 | 12/2010 |
| GB | 2306171 A | 4/1997 |
| KR | 1462545 | 11/2014 |
| WO | WO 92/01481 A1 | 2/1992 |
| WO | WO 2015/071154 | 5/2015 |
| WO | WO 2015/123329 A1 | 8/2015 |

OTHER PUBLICATIONS

International Search Report and Written Opinion for International Application No. PCT/US2015/015461, 10 pages (dated May 22, 2015).

International Search Report and Written Opinion for International Application No. PCT/US2017/063760, 14 pages (dated Feb. 23, 2018).

Pankratov, V.A., et al., "Polytriazines," *Russian Chemical Reviews*, 41(1):66-82 (1972).

* cited by examiner

*Primary Examiner* — Christopher M Rodd
(74) *Attorney, Agent, or Firm* — Eric D. Babych; Barnes & Thornburg LLP

(57) ABSTRACT

Scavenging compounds and compositions useful in reducing sulfide emissions from polymer treated asphalt, such as polyphosphoric acid, are disclosed. The scavengers include hexamethyl-enetetramine, water-free triazine, and water-free 1,3,5-triazine derivatives of formula I. Methods of using the compositions to reduce hydrogen sulfide emissions from asphalt are also disclosed.

20 Claims, No Drawings

HYDROGEN SULFIDE SCAVENGERS FOR POLYMER TREATED ASPHALT

TECHNICAL FIELD

The present disclosure relates generally to scavengers of sulfur-based species, and more particularly to compounds that scavenge hydrogen sulfide and/or mercaptan vapors released from polymer modified (treated) asphalt including, but not limited to, polyphosphoric acid.

BACKGROUND

Asphalt is commonly used in the construction and paving of roads. Asphalt is a mixture of aggregate material, such as sand, gravel, and crushed stone, with hot bitumen. The bitumen coats the aggregate material to give the asphalt, which may be spread as a uniform layer upon a road bed and compacted and smoothed with heavy rolling equipment.

Asphalt invariably contains sulfur. The amount of sulfur will depend on the origin of the crude oil, as well as the processes used to refine the crude oil, into asphalt. The sulfur may exist in different forms. For example, sulfur may be in the form of hydrogen sulfide. Hydrogen sulfide, or dihydrogen sulfide, is a chemical compound with the formula $H_2S$. It is a colorless, poisonous, flammable gas with the characteristically regarded foul odor.

Hydrogen sulfide may be released form asphalt, in particular when the asphalt is heated to a certain temperature. For example, hydrogen sulfide results from the dehydrogenation reactions that occur between bitumen and sulfur at the hot mixing temperatures, for example temperatures greater than 140° C. Hydrogen sulfide emissions are regulated. Therefore, there exists a need to reduce the amount of hydrogen sulfide in asphalt.

A variety of polymers are used to modify asphalt. The degree to which a polymer improves an asphalt's properties depends on the compatibility of the polymer and the asphalt; e.g., a polymer that does not separate in a mixture of asphalt and polymer during storage. Highly compatible or compatibilized polymers are more effective in providing property improvements. An extensive range of additives have been used for the purpose of "crosslinking" polymers and asphalts, thereby rendering the mixture compatible. For example, sulfur is a well-known crosslinking agent.

Polyphosphoric acid ($H_{n+2}P_nO_{3n+1}$) is a polymer of orthophosphoric acid ($H_3PO_4$). Polyphosphoric acid offered commercially is a mixture of orthophosphoric acid with pyrophosphoric acid, triphosphoric and higher acids. Superphosphoric acid is a similar mixture sold at 105% $H_3PO_4$. Other grades of phosphoric acid may contain water, but are not typically used in asphalt modification. This eliminates issues of foaming and corrosion at the refinery or terminal. PPA's major applications are surfactant production, water treatment, pharmaceutical synthesis, pigment production, flame proofing, metals finishing and asphalt modification. This circular will specifically discuss the use of PPA as an asphalt modification.

PPA has been widely used in refineries to modify the performance properties of asphalt. Due to its strong acidity, however, the PPA would revert most $H_2S$ scavengers and allow undesirable release the hydrogen sulfide from scavenger treated asphalt.

Accordingly, the present disclosure provides for a reduced or low release of hydrogen sulfide during the preparation of asphalt, as well as in the final asphalt material.

BRIEF SUMMARY

In one aspect a composition is disclosed that includes (a) asphalt or an asphalt mix further comprising polyphosphoric acid; and (b) a sulfide scavenging agent selected from the group consisting of: hexamethylenetetramine, water-free triazine, and 1,3,5-triazine derivatives of formula I

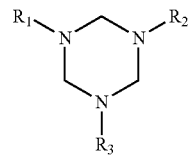

where each of $R^1$, $R^2$, and $R^3$ is independently selected from straight or branched $C_1$-$C_{30}$ alkyl, hydroxyl substituted straight or branched $C_1$-$C_{30}$ alkyl, straight or branched $C_1$-$C_{30}$ alkyl substituted with straight or branched $C_1$-$C_{30}$ alkoxy.

In another aspect, a method of reducing hydrogen sulfide emission from asphalt is disclosed that includes combining polyphosphoric acid treated asphalt or asphalt mix with a sulfide scavenging agent, the sulfide scavenging agent selected from the group consisting of: hexamethylenetetramine, water-free triazine, and 1,3,5-triazine derivatives of formula I

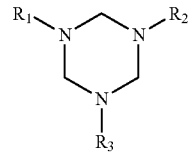

where each of $R^1$, $R^2$, and $R^3$ is independently selected from straight or branched $C_1$-$C_{30}$ alkyl, hydroxyl substituted straight or branched $C_1$-$C_{30}$ alkyl, straight or branched $C_1$-$C_{30}$ alkyl substituted with straight or branched $C_1$-$C_{30}$ alkoxy.

In some embodiments, the scavenger is of formula I, and each of $R^1$, $R^2$, and $R^3$ is independently selected from straight or branched $C_6$-$C_{30}$ alkyl, hydroxyl substituted straight or branched $C_6$-$C_{30}$ alkyl, straight or branched $C_6$-$C_{30}$ alkoxy substituted with straight or branched $C_1$-$C_{30}$ alkoxy.

In some embodiments, the scavenger is of formula I, and each of $R^1$, $R^2$, and $R^3$ is selected from $C_1$-$C_9$ straight or branched alkyl.

In some embodiments, the scavenger is of formula I, and each of $R^1$, $R^2$, and $R^3$ is the same.

In some embodiments, the scavenger is of formula I, and at least one of $R^1$, $R^2$, and $R^3$ is different from the other $R^2$, and $R^3$.

In some embodiments, $R^1$ is —$CH_2CH_2OH$, $R^2$ is —$CH_2CH_2OH$, and $R^3$ is —$CH_2CH_2OH$.

In some embodiments, the scavenger is hexamethylenetetramine.

In some embodiments, the scavenger is water-free triazine.

In some embodiments, the water-free triazine further comprises a low volatile polar solvent. In some embodiments, the low volatile polar solve is selected from diethylene glycol, 2-butoxyethanol, propylene glycol, monoethanol amine, and mixtures of the same.

In some embodiments, the polyphosphoric acid is present in the asphalt or asphalt mix at about 1 wt. %.

DETAILED DESCRIPTION

The present disclosure is related to a family of sulfide scavengers for use in PPA-treated asphalt, and the preparation thereof. The scavengers are particularly efficient at reducing hydrogen sulfide emissions of PPA-treated asphalt. The present disclosure is directed to a composition comprising PPA-treated asphalt with one or more sulfide scavengers. The present disclosure is also directed to a method of reducing hydrogen sulfide emission from PPA-treated asphalt, and the preparation thereof Unless expressly stated to the contrary, use of the term "a" is intended to include "at least one" or "one or more." For example, "a scavenger" is intended to include "at least one scavenger" or "one or more scavengers."

Any ranges given either in absolute terms or in approximate terms are intended to encompass both, and any definitions used herein are intended to be clarifying and not limiting. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges (including all fractional and whole values) subsumed therein.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not. In accordance with the present disclosure, the phrases "consist essentially of," "consists essentially of," "consisting essentially of," and the like limit the scope of a claim to the specified materials or steps and those materials or steps that do not materially affect the basic and novel characteristic(s) of the claimed invention.

The term "alkyl" as used herein, refers to a hydrocarbon radical with a defined number of carbon atoms (i.e., 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30 carbons). Branched alkyl groups include, but are not limited to, sec-butyl, tert-butyl, isobutyl, isopentyl, neopentyl, 1-methylbutyl, 2-methylbutyl, 1,1-dimethylpropyl, 1,2-dimethylpropyl, 1-ethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1,1,2-trimethylpropyl, 1,2,2-trimethylpropyl, 1-ethylbutyl, 2-ethylbutyl, 1-methylhexyl, 2-methylhexyl, 3-methylhexyl, 4-methylhexyl, 5-methylhexyl, 1,1-dimethylpentyl, 1,2-dimethylpentyl, 1,3-dimethylpentyl, 1,4-dimethylpentyl, 2,2-dimethylpentyl, 2,3-dimethylpentyl, 2,4-dimethylpentyl, 3,3-dimethylpentyl, 3,4-dimethylpentyl, 4,4-dimethylpentyl, 1,1,2-trimethylbutyl, 1,1,3-trimethylbutyl, 1,2,2-trimethylbutyl, 1,2,3-trimethylbutyl, 1,3,3-trimethylbutyl, 2,2,3-trimethylbutyl, 2,3,3-trimethylbutyl, 1,1,2,2-tetramethylpropyl, 1-ethylpentyl, 2-ethylpentyl, 3-ethylpentyl, 1-ethyl-1-methylbutyl, 1-ethyl-2-methylbutyl, 1-ethyl-3-methylbutyl, 2-ethyl-1-methylbutyl, 2-ethyl-2-methylbutyl, 2-ethyl-3-methylbutyl, 1-propylbutyl, 1,1-diethylpropyl, etc.

In some embodiments, the number of carbon atoms for the alkyl group is between 6 and 30. In some embodiments, the number of carbon atoms for the alkyl group is between 6 and 20. In some embodiments, the number of carbon atoms for the alkyl group is between 6 and 15. In some embodiments, the number of carbon atoms for the alkyl group is between 6 and 10. In some embodiments, the number of carbon atoms for the alkyl group is between 6 and 8.

The term "alkoxyl" as used herein, refers to a ether radical with a defined number of carbon atoms (i.e., 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30 carbons). Branched alkyl groups include, but are not limited to, secbutoxy, tert-butoxy, isobutoxy, isopentoxy, neopentoxy, 1-methylbutoxy, 2-methoxybutoxy, 1,1-dimethylpropoxy, 1,2-dimethylpropoxy, 1-ethylpropoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1,1,2-trimethylpropoxy, 1,2,2-trimethylpropoxy, 1-ethylbutoxy, 2-ethylbutoxy, 1-methylhexoxy, 2-methylhexoxy, 3-methylhexoxy, 4-methylhexoxy, 5-methylhexoxy, 1,1-dimethylpentoxy, 1,2-dimethylpentoxy, 1,3-dimethylpentoxy, 1,4-dimethylpentoxy, 2,2-dimethylpentoxy, 2,3-dimethylpentoxy, 2,4-dimethylpentoxy, 3,3-dimethylpentoxy, 3,4-dimethylpentoxy, 4,4-dimethylpentoxy, 1,1,2-trimethylbutoxy, 1,1,3-trimethylbutoxy, 1,2,2-trimethylbutoxy, 1,2,3-trimethylbutoxy, 1,3,3-trimethylbutoxy, 2,2,3-trimethylbutoxy, 2,3,3-trimethylbutoxy, 1,1,2,2-tetramethylpropoxy, 1-ethylpentoxy, 2-ethylpentoxy, 3-ethylpentoxy, 1-ethyl-1-methylbutoxy, 1-ethyl-2-methylbutoxy, 1-ethyl-3-methylbutoxy, 2-ethyl-1-methylbutoxy, 2-ethyl-2-methylbutoxy, 2-ethyl-3-methylbutoxy, 1-propylbutoxy, 1,1-diethylpropoxy, etc.

In some embodiments, the number of carbon atoms for the alkyl portion of the alkoxy group is between 6 and 30. In some embodiments, the number of carbon atoms for the alkyl group is between 6 and 20. In some embodiments, the number of carbon atoms for the alkyl group is between 6 and 15. In some embodiments, the number of carbon atoms for the alkyl group is between 6 and 10. In some embodiments, the number of carbon atoms for the alkyl group is between 6 and 8.

As used herein, the term "asphalt" refers to any of a variety of materials that are solid or semisolid at room temperature and which gradually liquefy when heated, and in which the predominant constituents are naturally occurring bitumens (or kerogens) or which are bitumen like materials obtained as residue in petroleum refining. It is expressly contemplated that asphalt as used herein includes what ASTM defines as asphalt: a dark brown to black cementitious material in which the predominant constituents are bitumens that occur in nature or are obtained in petroleum processing. Asphalts characteristically contain very high molecular weight hydrocarbons called asphaltenes. These are essentially soluble in carbon disulfide, and aromatic and chlorinated hydrocarbons. Bitumen is a generic term defined by the ASTM as a class of black or dark-colored cementitious substances, natural or manufactured, composed principally of high molecular weight hydrocarbons, of which asphalts, tars, pitches and asphaltenes are typical. The ASTM further classifies asphalts or bituminous materials as solids, semi-solids, or liquids using a penetration test for consistency or viscosity. In this classification, solid materials are those having a penetration of not more than 1 millimeter when a load of 100 grams is applied for 5 seconds while at 25° C., and semi-solids are those having a penetration of more than 1 millimeter when a load of 50 grams is applied for 5 seconds while at 25° C. Semi-solid and liquid asphalts predominate in commercial practice today. For example, any asphalt bottoms fraction, as well as naturally occurring asphalts, tars and pitches and may be used interchangeably herein with the term "bitumen." The term "asphaltic concrete" means asphalt used as a binder with appropriate aggregate added, typically for use as a paving material.

The term "bottoms fraction" refers to a crude fraction having a flash point of about 70° F. or greater.

The term "water-free" as used herein, refers to compositions where the amount of water present is less than about 5 weight percent.

Compositions

The compositions disclosed herein include asphalt or an asphalt mix that has been treated with polyphosphoric acid. The composition also includes a sulfide scavenging agent. The sulfide scavenging agent is selected from hexamethylenetetramine, water-free triazine, and 1,3,5-triazine derivatives of formula I

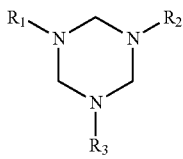

Formula I where each of $R^1$, $R^2$, and $R^3$ is independently selected from straight or branched $C_1$-$C_{30}$ alkyl, hydroxyl substituted straight or branched $C_1$-$C_{30}$ alkyl, straight or branched $C_1$-$C_{30}$ alkyl substituted with straight or branched $C_1$-$C_{30}$ alkoxy.

In some embodiments, the sulfide scavenging agent is hexamethylenetetramine, sometimes abbreviated (HMTA) which has the structure:

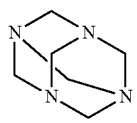

Hexamethylenetetramine.

In some embodiments, the sulfide scavenging agent is water-free triazine. Triazine has the structure:

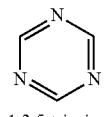

1,3,5-triazine

In some embodiments, the sulfide scavenging agent is a 1,3,5-triazine derivatives of formula I

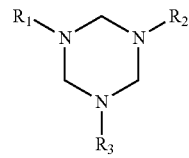

having the substituents for $R^1$, $R^2$, and $R^3$ defined above. In some embodiments, each of $R^1$, $R^2$, and $R^3$ is independently selected from straight or branched $C_1$-$C_{30}$ alkyl. In some embodiments, each of each of $R^1$, $R^2$, and $R^3$ is independently selected from straight or branched $C_6$-$C_{30}$ alkyl.

In some embodiments, each of $R^1$, $R^2$, and $R^3$ is independently hydroxyl substituted straight or branched $C_1$-$C_{30}$ alkyl. In some embodiments, each of $R^1$, $R^2$, and $R^3$ is independently hydroxyl substituted straight or branched $C_6$-$C_{30}$ alkyl.

In some embodiments, each of $R^1$, $R^2$, and $R^3$ is independently straight or branched $C_1$-$C_{30}$ alkyl substituted with straight or branched $C_1$-$C_{30}$ alkoxy. In some embodiments, each of $R^1$, $R^2$, and $R^3$ is independently straight or branched $C_6$-$C_{30}$ alkyl substituted with straight or branched $C_1$-$C_{30}$ alkoxy. In some embodiments, each of $R^1$, $R^2$, and $R^3$ is independently straight or branched $C_6$-$C_{30}$ alkyl substituted with straight or branched $C_6$-$C_{30}$ alkoxy.

In some embodiments, each of $R^1$, $R^2$, and $R^3$ is the same. In some embodiments, $R^1$ is different from $R^2$ and $R^3$. In some embodiments, $R^1$ and $R^2$ are the same. In some embodiments, $R^1$ and $R^2$ are the same and are also different from $R^3$. In some embodiments, $R^1$ is different from $R^2$ and $R^3$, and $R^2$ is different from $R^3$.

The asphalt composition includes polyphosphroric acid. Such acid modification of the asphalt generally results in asphalt compositions that exhibit improved low temperature performance, for example. The asphalt composition includes less than or equal to about 5 wt. % acid. In some emobidments, the asphalt composition includes less than or equal to about 3 wt. % acid. In some embodiments, the asphalt composition includes less than about 2.5 wt. % acid. In some embodiments, the asphalt composition includes less than about 1 wt. % acid and may include from about 0.01 wt. % to about 1 wt. % acid, or from about 0.05 wt. % to about 1 wt. % acid or from about 0.1 wt. % to about 1 wt. % acid, for example.

The compositions disclosed herein can optionally include one or more additives. Suitable additives include, but are not limited to, asphaltene inhibitors, paraffin inhibitors, corrosion inhibitors, scale inhibitors, emulsifiers, water clarifiers, dispersants, emulsion breakers, gas hydrate inhibitors, biocides, pH modifiers, surfactants, solvents, and combinations thereof The asphalt composition may further include additives, such as sulfonating agents, crosslinking agents or combinations thereof, for example. The asphalt composition may include from about 0.001 wt. % to about 5 wt. % of total additives or from about 0.01 wt. % to about 3 wt. % of total additives, for example.

The crosslinking agents may be activators (e.g., zinc oxide), accelerators, such as sulfur compounds (e.g., mercaptobenzothizole (MBT)) or both accelerators and activators, such as a zinc salt of MBT, for example. In one embodiment, the crosslinking agent is a metal oxide.

The additives may further include unsaturated functional monomers, unsaturated carboxylic acids, unsaturated dicarboxylic acids, unsaturated anhydrides, unsaturated esters, unsaturated amides or combinations thereof, for example.

Preparation Methods

Generally, the compositions are made with water-free sulfide scavengers and to facilitate handling of polyphosphoric acid treated asphalt and asphalt mixtures at a temperature of greater than about 250° C. or less. In some embodiments, the temperature of the asphalt or asphalt mixture is less than about 200° C. In some embodiments, the temperature of the asphalt or asphalt mixture is less than about 150° C. In some embodiments, the temperature of the asphalt or asphalt mixture is less than about 100° C. In some embodiments, the temperature of the asphalt or asphalt mixture is less than about 90° C.

Illustrative methods of forming such asphalt compositions are described below, but in no way limit the methods that may be utilized to form such compositions. For example, in one embodiment, asphalt is heated in a first mixing vessel to a temperature of from about 140° C. to 205° C. The asphalt concentrate may then be transferred to a second mixing vessel or remain in the first mixing vessel.

Polyphosphoric acid is added. The acid is added in a timed release sufficient to avoid foaming, such as from about 20 minutes to about 1 hour, for example. The acid, however, can be added at any point in the process and to any vessel or conduit in the process. For example, the acid can be added to a first or second mixing vessel or to a conduit operably connecting the first and second mixing vessels.

Sulfide scavenger is added. The scavenger can be added before the polyphosphoric acid is added or thereafter. The addition of the sulfur scavenger under agitation typically for 15 minutes to 10 hours. The concentration of the sulfur scavenger varies according to the workability of the mixture, and typically could range from 5% wt to 90% and most typically from 20 to 60% wt. The rate of addition into the asphalt or bitumen is proportionel to its solid content and varies from 0.01 to 10%, preferably from 0.1 to 0.5% wt. Other process control steps include thorough agitation and mixing to assure mixture of the scavenger with the asphalt mixture.

Product Applications

The asphalt compositions described herein can be used for many applications, such as road paving, sealing, water proofing, asphalt cement and/or roofing, for example.

The compounds, compositions, methods, and processes will be better understood by reference to the following examples, which are intended as an illustration of and not a limitation upon the scope of the present disclosure.

EXAMPLES

Sulfide emissions from polyphosphoric acid treated asphalt were measured to examine the effectiveness of various sulfide scavengers. All $H_2S$ levels reported below and observed were measured by modified ASTM D5705 at annotated temperature and residual time.

The $H_2S$ testing was conducted by adding 1 wt % PPA to asphalt and keeping the mixture at 300° F. for 24 hours to allow any $H_2S$ release. At the end of this 24 hour period, the vapor phase $H_2S$ concentration of sample was determined and recorded as initial $H_2S$. The scavenger was then added to this PPA treated asphalt sample, and the sample was kept at 300° F. for another 24 or 48 hours. The vapor phase $H_2S$ after this 24 or 48 hour period was measured and reported as final $H_2S$.

Tested hydrogen sulfide scavengers included hexamethylenetetramine (HMTA)—Table 1 and water-free triazine—Table 2.

TABLE 1

Observed $H_2S$ scavenging on 1 wt % PPA treated asphalt at 148° C. using HMTA.

| H2S Scavenger | Residual Time/hrs | Initial H2S/ppm | Rxn Ratio | Dosage/g | Final H2S/ppm |
| --- | --- | --- | --- | --- | --- |
| HMTA | 48 | 13000 | Blank | / | / |
| | 48 | 13000 | 0.1 | 0.65 | 65 |
| | 48 | 13000 | 0.2 | 1.3 | 5 |
| | 48 | 13000 | 0.5 | 3.25 | 15 |
| | 48 | 13000 | 1 | 6.5 | 0 |

TABLE 2

Observed scavenging of $H_2S$ on 1 wt % PPA treated asphalt at 148° C. using water-free triazine.

| H2S Scavenger | Residual Time/hrs | Initial H2S/ppm | Rxn Ratio | Dosage/ppm | Final H2S/ppm |
| --- | --- | --- | --- | --- | --- |
| Water Free Triazine | 24 | 7500 | Blank | / | / |
| | 24 | 7500 | 0.25 | 1875 | 400 |
| | 24 | 7500 | 0.5 | 3750 | 60 |
| | 24 | 7500 | 1 | 7500 | 20 |

What is claimed is:

1. A composition, comprising:
   (a) asphalt or an asphalt mix further comprising polyphosphoric acid; and
   a water-free triazine sulfide scavenging agent.

2. The composition of claim 1, wherein the water-free triazine further comprises a low volatile polar solvent.

3. The composition of claim 2, wherein the low volatile polar solve is selected from diethylene glycol, 2-butoxyethanol, propylene glycol, monoethanol amine, and mixtures of the same.

4. The composition of claim 1, wherein the polyphosphoric acid is present in the asphalt or asphalt mix at about 1 wt. %.

5. A method of reducing hydrogen sulfide emission from asphalt, comprising:
   combining polyphosphoric acid treated asphalt or asphalt mix with a sulfide scavenging agent, the sulfide scavenging agent selected from the group consisting of: water-free triazine, 1,3,5-triazine derivatives of formula I, and any combination thereof, wherein formula I comprises:

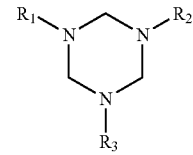

where each of $R^1$, $R^2$, and $R^3$ is independently selected from straight or branched $C_1$-$C_{30}$ alkyl, hydroxyl substituted straight or branched $C_1$-$C_{30}$ alkyl, straight or branched $C_1$-$C_{30}$ alkyl substituted with straight or branched $C_1$-$C_{30}$ alkoxy.

6. The method of claim 5, wherein the scavenger is of formula I, and each of $R^1$, $R^2$, and $R^3$ is independently selected from straight or branched $C_6$-$C_{30}$ alkyl, hydroxyl substituted straight or branched $C_6$-$C_{30}$ alkyl, straight or branched $C_6$-$C_{30}$ alkoxy substituted with straight or branched $C_1$-$C_{30}$ alkoxy.

7. The method of claim 5, wherein the scavenger is of formula I, and each of $R^1$, $R^2$, and $R^3$ is the same.

8. The method of claim 5, wherein the scavenger is of formula I, and at least one of $R^1$, $R^2$, and $R^3$ is different from the other $R^1$, $R^2$, and $R^3$.

9. The method of claim 5, wherein $R^1$ is —$CH_2CH^2OH$, $R^2$ is —$CH_2CH_2OH$, and $R^3$ is —$CH_2CH_2OH$.

10. The method of claim 5, wherein the scavenger is water-free triazine.

11. The method of claim 5, wherein the water-free triazine further comprises a low volatile polar solvent.

12. The composition of claim 1, further comprising hexamethylenetetramine.

13. The method of claim 5, further comprising combining the polyphosphoric acid treated asphalt or the asphalt mix with hexamethylenetetramine.

14. A composition, comprising:
(a) asphalt or an asphalt mix further comprising polyphosphoric acid; and
(b) a sulfide scavenging agent selected from the group consisting of: water-free triazine, a 1,3,5-triazine derivative of formula I, and any combination thereof, wherein formula I comprises:

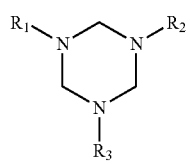

wherein each of $R^1$, $R^2$, and $R^3$ is independently selected from straight or branched $C_1$-$C_{30}$ alkyl, hydroxyl substituted straight or branched $C_1$-$C_{30}$ alkyl, straight or branched $C_1$-$C_{30}$ alkyl substituted with straight or branched $C_1$-$C_{30}$ alkoxy.

15. The composition of claim 14, wherein the scavenger is of formula I, and each of $R^1$, $R^2$, and $R^3$ is independently selected from straight or branched $C_6$-$C_{30}$ alkyl, hydroxyl substituted straight or branched $C_6$-$C_{30}$ alkyl, straight or branched $C_6$-$C_{30}$ alkoxy substituted with straight or branched $C_1$-$C_{30}$ alkoxy.

16. The composition of claim 14, wherein the scavenger is of formula I, and each of $R^1$, $R^2$, and $R^3$ is selected from $C_1$-$C_9$ straight or branched alkyl.

17. The composition of claim 14, wherein the scavenger is of formula I, and each of $R^1$, $R^2$, and $R^3$ is the same.

18. The composition of claim 14, wherein the scavenger is of formula I, and at least one of $R^1$, $R^2$, and $R^3$ is different from the other $R^1$, $R^2$, and $R^3$.

19. The composition of claim 14, wherein $R^1$ is —$CH^2CH_2OH$, $R^2$ is —$CH_2CH_2OH$, and $R^3$ is —$CH_2CH_2OH$.

20. The composition of claim 14, wherein the polyphosphoric acid is present in the asphalt or asphalt mix at about 1 wt. %.

* * * * *

UNITED STATES PATENT AND TRADEMARK OFFICE
CERTIFICATE OF CORRECTION

PATENT NO.        : 10,544,282 B2                                    Page 1 of 1
APPLICATION NO.   : 15/826408
DATED             : January 28, 2020
INVENTOR(S)       : Xiaowei Tong et al.

It is certified that error appears in the above-identified patent and that said Letters Patent is hereby corrected as shown below:

In the Claims

In Column 8, Line 59, Claim 5, please delete "$C_1$-$C_3o$" and insert --$C_1$-$C_{30}$--.

In Column 8, Line 61, Claim 5, please delete "$C_1$-$C_{30}$alkoxy." and insert --$C_1$-$C_{30}$ alkoxy.--.

In Column 8, Line 67, Claim 6, please delete "$C_1$-$C_{30}$alkoxy." and insert --$C_1$-$C_{30}$ alkoxy.--.

In Column 9, Line 6, Claim 9, please delete "—$CH_2CH^2OH$," and insert -- —$CH_2CH_2OH$,--.

In Column 10, Line 4, Claim 14, please delete "$C_1$-$C_{30}$alkyl" and insert --$C_1$-$C_{30}$ alkyl--.

In Column 10, Line 5, Claim 14, please delete "$C_1$-$C_{30}$alkoxy." and insert --$C_1$-$C_{30}$ alkoxy.--.

In Column 10, Line 12 (approx.), Claim 15, delete "$C_1$-$C_{30}$alkoxy." and insert --$C_1$-$C_{30}$ alkoxy.--.

In Column 10, Line 23 (approx.), Claim 19, please delete "—$CH^2CH_2OH$," and insert -- —$CH_2CH_2OH$,--.

Signed and Sealed this
Seventh Day of April, 2020

Andrei Iancu
*Director of the United States Patent and Trademark Office*